United States Patent [19]

Bartley

[11] Patent Number: 4,628,129

[45] Date of Patent: Dec. 9, 1986

[54] PROCESS FOR THE PREPARATION OF ETHYLENE GLYCOL

[75] Inventor: William J. Bartley, Charleston, W. Va.

[73] Assignee: Union Carbide Corporation, Danbury, Conn.

[21] Appl. No.: 697,927

[22] Filed: Feb. 4, 1985

[51] Int. Cl.$^4$ .................. C07C 29/136; C07C 31/20
[52] U.S. Cl. .................. 568/864; 502/243; 568/881; 568/885
[58] Field of Search .................. 568/864, 881, 885

[56] References Cited

U.S. PATENT DOCUMENTS

| | | | |
|---|---|---|---|
| 3,197,418 | 7/1965 | Maebashi et al. | 568/885 |
| 3,923,689 | 12/1975 | Broughton et al. | 502/418 |
| 4,112,245 | 9/1978 | Zehner et al. | 568/864 |
| 4,119,656 | 10/1978 | Poutsma et al. | 518/715 |

OTHER PUBLICATIONS

Koritala, "J. Am. Oil Chem. Soc.", vol. 45 (1968), pp. 197–200.
Corson et al, "J. Phys. Chem.", vol. 45 (1941), pp. 431–440.

*Primary Examiner*—J. E. Evans
*Attorney, Agent, or Firm*—Steven T. Trinker

[57] ABSTRACT

A process for the preparation of ethylene glycol by the catalytic hydrogenation of at least one of di(lower alkyl) oxalate and lower alkyl glycolate in the presence of a hydrogenation catalyst comprising a carrier, which catalyst is suitable for the hydrogenation of alkyl oxalate and alkyl glycolate to ethylene glycol, wherein the carrier has a leachable iron content not greater than about 0.03%, by weight of the carrier.

24 Claims, No Drawings

PROCESS FOR THE PREPARATION OF ETHYLENE GLYCOL

This invention relates to an improved process for the preparation of ethylene glycol by the vapor phase catalytic hydrogenation of at least one of di(lower alkyl) oxalate and lower alkyl glycolate in the presence of a hydrogenation catalyst comprising a carrier, which catalyst is suitable for the hydrogenation of alkyl oxalate and alkyl glycolate to ethylene glycol. More particularly, this invention relates to the catalytic hydrogenation of di(lower alkyl) oxalate to produce ethylene glycol using catalysts comprising carriers having a leachable iron ($Fe^{+2}$ and/or $Fe^{+3}$) content not greater than about 0.03%, by weight of the carrier.

INTRODUCTION TO ETHYLENE GLYCOL

Ethylene glycol is a valuable commercial chemical and finds application in deicing fluids, antifreeze, hydraulic fluids, manufacture of alkyd resins, solvents and the manufacture of polyesters. As disclosed in Kirk-Othmer, Encyclopedia of Chemical Technology, 3rd Edition, ethylene glycol is commercially made by the hydrolysis of ethylene oxide which, in turn, is made by the catalytic epoxidation of ethylene using air or oxygen. However, several problems, particularly raw material supply, are associated with these commercial processes.

First, ethylene is made commercially from natural gas liquids or naphthas. Second, in the catalytic epoxidation of ethylene in commercial facilities, the selectivity to ethylene oxide is usually less than 80 percent, with carbon dioxide being the primary by-product. Finally, the hydrolysis of ethylene oxide to ethylene glycol in conventional processes coproduces diethylene glycol and triethylene glycol.

It has been proposed to use synthesis gas, i.e., mixtures of carbon monoxide and hydrogen, as alternative starting materials for the preparation of ethylene glycol, thus reducing dependency on ethylene and in turn the feed stocks required to produce ethylene. In some of these processes, the synthesis gas is reacted to form di(alkyl) oxalates which are then hydrogenated to form the desired ethylene glycol. This hydrogenation is especially difficult since the hydrogenation must be sufficient to reduce the ester radical, yet avoid over hydrogenation to ethanol and other by-products. Moreover, it can be readily appreciated that hydrogenation reactions can yield a spectrum of products, due to both under and over hydrogenation. These by-products not only reduce the efficiency to ethylene glycol, but also can present troublesome impurities that must be removed from the ethylene glycol.

U.S. Pat. No. 4,112,245 to Zehner, et al., discloses the preparation of ethylene glycol by the vapor phase catalytic hydrogenation of dialkyl oxalate in the presence of a copper-containing catalyst. The patent states that by utilizing an oxalate feed which has been essentially desulfurized, undesirable side reactions are minimized and undesirable sulfur contamination of the hydrogenation catalyst and loss of catalyst activity are reduced. An oxalate ester feed with less than 0.4 ppm sulfur and the use of hydrogen that is essentially free of sulfur is recommended. However, this patent does not disclose any significance to catalysts comprising carriers. In particular, this reference does not disclose any significance to the leachable iron content of the catalyst carrier, nor to iron as a factor in the hydrogenation of dialkyl oxalates to ethylene glycol.

INTRODUCTION TO CATALYST CARRIERS

It is often desired to employ catalysts that comprise carriers. Among the benefits that are provided by catalyst carriers are reducing the amount of the catalytically-active species required, providing the catalyst in a more easily handled form, and facilitating the use of the catalyst in commercial-sized reactors without, for example, undue pressure drops or poor distribution of reactants throughout the reaction bed.

Carriers can be composed of various materials including silica. Moreover, the extraneous matter present in a given carrier may vary widely in both nature and quantity. Unfortunately, this same extraneous matter can adversely affect the performance of the catalyst, even though the carrier, itself, may be inert. The selection of suitable carriers has thus proven to be an empirical and complex task.

Silica catalyst carriers for the above-described processes, can physically degrade under process conditions resulting in the production of fines and causing excessively high pressure drops across high pressure reactor catalyst beds. These pressure drops can result in intermittent shut-downs, high catalyst replacement costs and consequent loss of production. Therefore, maintaining the crush strength of a carrier over the several hundred hours of use under process reaction conditions is important in order to avoid these potential problems.

R. K. Isler, "The Chemistry of Silica", John Wiley, New York, 1979, p. 549, discloses that alkali metals promote silica sintering through a labilization of the Si-O-Si bonds. Mertens and Fripiat, *J. Colloid and Interface Sci.*, 42:169 (1973), disclose that methanol esterifies the silica surface hydroxyl groups. Neither makes reference to the volatilization of silica carriers.

The alkali metals which are frequently components of silica carriers, as received from the manufacturer, are sodium and potassium with lithium, rubidium and cesium being present to a lesser extent.

REMOVAL OF EXTRANEOUS MATTER FROM CATALYST CARRIERS

Various processes are known for the partial removal of iron and other matter from materials, such as carriers. For example, U.S. Pat. No. 3,923,689 discloses a method for reducing the iron content of materials such as charcoal, active carbon, molecular sieves, activated clays, activated silica and activated alumina. This method involves treating the material with an acidic solution containing a suitable reducing agent. The procedure is recommended for carriers containing iron that are to be used in a process in which iron impurities would be objectionable. While this patent generally discloses the removal of iron from carriers, it does not specifically disclose processes that would benefit from such removal.

U.S. Pat. No. 4,087,383 entitled "Method for Acid Treating Solid Supports" discloses a process for preparing support or carrier materials for catalytic use. The carrier material is prepared by pre-soaking a porous, solid particulate carrier in an organic liquid, immersing the carrier without drying in a dilute acid solution for a given time interval, then drying and calcining the carrier. After calcination, the carrier is impregnated with the active catalyst precursor material. This patent contains a general suggestion that the activity of many catalysts can be altered, and improved, by an acid treatment of the carrier material. However, this broad general statement teaches nothing about the manner or processes in which this activity can be improved, and it makes no reference to the catalytic hydrogenation of oxalate esters to ethylene glycol.

Koritala, Selective Hydrogenation of Soybean Oil III. Copper-Exchanged Molecular Sieves and Other Supported Catalysts, *J. Am. Oil Chem. Soc.* 45:197 (1968), for example, discloses processes that benefit from removal of iron or other matter from carriers. This publication is specific to improved selectivity and activity in the reduction of linolenyl groups in soybean oil when catalyst carriers, e.g., silica, are treated (washed) with hydrochloric acid for iron removal. However, this reaction involves reactants and reaction conditions significantly different from those employed in the production of ethylene glycol by the hydrogenation of di(-lower alkyl) oxalates.

Corson, et al., Activation and Poisoning of Copper Hydrogenation Catalysts, *J. Phys. Chem.* 45:431 (1941) disclose that sodium sulfate is a strong poison for nickel-promoted copper hydrogenation catalysts. However, this article "emphasizes the extreme delicacy of catalytic processes and the necessity of careful definition of purity before drawing conclusions as to the catalytic properties of any particular element or catalyst."

Thus, while the prior art has in general terms recognized the importance of a carrier's composition including extraneous matter, there has been a general failure in the prior art to recognize the importance of the carrier's materials of construction and extraneous matter in reference to particular catalytic reactions, and certainly no guidance has been provided toward selecting advantageous catalysts for the hydrogenation of di(lower alkyl) oxalates to prepare ethylene glycol.

SUMMARY OF THE INVENTION

This invention relates to a process for the preparation of ethylene glycol comprising the steps of contacting, in the vapor phase and under glycol-forming hydrogenation conditions, hydrogen with at least one of di(lower alkyl) oxalate and lower alkyl glycolate in the presence of a catalytically-effective amount of a hydrogenation catalyst comprising a carrier, which catalyst is suitable for the hydrogenation of alkyl oxalate and alkyl glycolate to ethylene glycol, wherein the carrier has a leachable iron content not greater than about 0.03%, by weight of the carrier.

Aspects of this invention relate to the above-described process wherein the leachable iron content of said carrier has been reduced by treatment with an aqueous acid solution, from a value greater than about 0.03%, by weight of the carrier, to a value not greater than about 0.03%, by weight of the carrier.

Further aspects of this invention relate to the above-stated process wherein the carrier has a leachable sulfur, expressed as sulfate, content not greater than about 0.04%, by weight of the carrier. Additionally, this invention relates to the above-described process wherein the leachable sulfur, expressed as sulfate, content of said carrier has been reduced by treatment with an aqueous acid solution, from a value greater than about 0.04%, by weight of the carrier, to a value not greater than about 0.04%, by weight of the carrier.

Additional aspects of this invention relate to the above-stated process wherein the carrier has a leachable alkali metal content not greater than about 0.03%, by weight of the carrier. In some further aspects of this invention the leachable alkali metal content of said carrier has been reduced by treatment with an aqueous acid solution sufficient to enhance the physical stability of the catalyst in the process, e.g., often the reduction is from a value greater than about 0.03%, by weight of the carrier, to a value not greater than about 0.03%, by weight of the carrier.

In some preferred aspects, this invention relates to the above-stated process, wherein the carrier has a leachable iron content not greater than about 0.03%, by weight of the carrier, a leachable sulfur content, expressed as sulfate, not greater than about 0.04%, by weight of the carrier, and a leachable alkali metal content not greater than about 0.03%, by weight of the carrier. Often, in these preferred carriers the leachable iron content, the leachable sulfur, expressed as sulfate, content, and the leachable alkali metal content has been reduced by treatment with an aqueous acid solution, from values greater than about 0.03%, about 0.04%, and about 0.03%, respectively, by weight of the carrier, to values not greater than about 0.03%, about 0.04%, and about 0.03%, respectively, by weight of the carrier.

By utilizing a catalyst carrier having a leachable iron ($Fe^{+2}$ and/or $Fe^{+3}$) content not greater than about 0.03%, by weight of the carrier, it has been found that the activity of the hydrogenation catalysts in the above-described process is significantly improved. Improvement also occurs by utilizing a catalyst carrier having a leachable sulfur, expressed as sulfate, content not greater than about 0.04%, by weight of the carrier.

It has been found that silica carriers having the aforementioned maximum leachable iron and/or sulfur concentrations permitted preparation of catalysts which were significantly more active in ethylene glycol production than those produced from silica carriers whose leachable iron and/or sulfur concentrations substantially exceeded those amounts. This increased activity may be accomplished either by the removal of iron and/or sulfur, which are commonly present in commercial carriers, or the selection of carriers already having iron and/or sulfur concentrations below the limits described above.

It has been found that the degradation of silica carriers is, at least in part, due to the attack of reactants and/or products, e.g., alkanols, under oxalate hydrogenation conditions. It has been found that degradation of such carriers under the conditions of the process can be significantly reduced by removal of alkali metal(s) from the carrier material.

While any suitable treatment of catalyst carriers may be utilized to obtain the desired maximum iron, sulfur, and/or alkali metal concentrations, it is believed that treatment with oxalic acid is especially useful. Using aqueous oxalic acid solutions, commercial catalyst carrier materials can be rendered suitable for use in accordance with the present invention. Specifically, their iron, sulfur and/or alkali metal concentrations can be reduced to below the desired levels and the catalysts prepared from them can exhibit enhanced activity in the above-described catalytic hydrogenation process.

DISCUSSION OF THE HYDROGENATION PROCESS

Ethylene glycol can be prepared by the vapor phase catalytic hydrogenation of a di(lower alkyl) ester of oxalic acid at elevated temperature and pressure.

An overall equation for the reaction is believed to be represented as follows:

$$\underset{\text{oxalate ester}}{ROOCCOOR} + 4H_2 \xrightarrow[\text{pressure}]{\text{catalyst heat +}} \underset{\text{ethylene glycol}}{HOCH_2CH_2OH} + 2ROH \text{ alkanol}$$

The hydrogenation of di(alkyl) oxalates is believed to proceed stepwise according to the following equations:

$$\underset{\text{di(alkyl) oxalate}}{ROOCCOOR} + 2H_2 \xrightarrow[\text{pressure}]{\text{catalyst heat +}} \underset{\text{alkyl glycolate}}{HOCH_2COOR} + ROH \text{ alkanol}$$

$$\underset{\text{alkyl glycolate}}{HOCH_2COOR} + 2H_2 \xrightarrow[\text{pressure}]{\text{catalyst heat +}} \underset{\text{ethylene glycol}}{HOCH_2CH_2OH} + ROH \text{ alkanol}$$

The first step involves the hydrogenation of one of the alkoxycarbonyl groups of a di(alkyl) oxalate to form an alkyl glycolate and the corresponding alkanol. In the second step, the remaining alkoxycarbonyl group is hydrogenated to produce ethylene glycol plus the corresponding alkanol.

The oxalate esters which may be hydrogenated in accordance with the processes of this invention conform to the general formula:

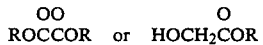

wherein R is a lower alkyl group. The preferred esters for use in the hydrogenation process for the preparation of ethylene glycol are those esters wherein R is an alkyl group containing from 1 to 4 carbon atoms. Especially preferred esters are dimethyl oxalate and diethyl oxalate.

In carrying out the hydrogenation reaction, the di(-lower alkyl) ester of oxalic acid is generally preheated and vaporized, with the conditions of the hydrogenation being selected to ensure that essentially all of the ester is in the vapor state when passed over the catalyst bed. Thus, the reaction zone is maintained at an elevated temperature and pressure sufficient for hydrogenation to ethylene glycol and for preventing condensation of the oxalate ester and the product ethylene glycol.

The processes, in accordance with the present invention, are carried out by passing vaporized oxalate ester, together with hydrogen over the catalyst maintained at a reaction zone temperature typically between about 150° C. and about 300° C. and preferably between about 180° C. and about 240° C. The molar ratio of hydrogen to oxalate ester passed to the reaction zone is usually at least sufficient on a stoichiometric basis for complete hydrogenation of the oxalate ester to ethylene glycol and is often between about 4:1 and 200:1 and preferably between about 10:1 and 100:1. A hydrogen pressure between about 1 bar and about 350 bars is frequently used and preferably the hydrogen pressure is between about 10 bars and about 100 bars. In advantageous aspects of the processes, the gas hourly space velocity (the total volume of the vaporous oxalate and hydrogen gaseous mixture, as calculated at ambient temperature and pressure, passed over a unit volume of hydrogenation catalyst bed per hour) is between about 2,000 hr.$^{-1}$ and about 25,000 hr.$^{-1}$ and preferably between about 5,000 hr.$^{-1}$ and about 15,000 hr.$^{-1}$. The liquid hourly space velocity of oxalate ester (calculated as the liquid volume of oxalate, expressed in liquid form per unit volume of hydrogenation catalyst which is passed over the catalyst) is typically maintained between about 0.1 hr.$^{-1}$ and about 3.0 hr.$^{-1}$ and preferably between about 0.5 hr.$^{-1}$ and about 2.0 hr.$^{-1}$. For convenience, as used herein, the oxalate liquid hourly space velocity is calculated prior to mixing with hydrogen and is based on a liquid rather than a gaseous volume.

In particularly attractive aspects of this invention, the percent conversion, calculated as the moles of oxalate in the feed minus the moles of oxalate recovered in the feed mixture after reaction divided by the moles of oxalate in the feed multiplied by 100, is maintained at greater than about 80% and preferably greater than about 95%. The percent conversion is a dependent variable, as the reaction temperature, the liquid hourly space velocity and other reaction variables are provided at sufficient interrelated values to obtain the desired conversion percent.

CATALYST AND ITS PREPARATION

The catalytically-active moieties deposited on the carrier may, in the broadest sense, include any moiety or mixture of moieties, capable of selectively hydrogenating esters to form hydroxyl substituted carbons such as the hydrogenation of di(alkyl)oxalate to form ethylene glycol. Therefore, a moiety exhibiting a relatively weak hydrogenation activity is preferred in order to maximize ethylene glycol production and minimize hydrogenolysis of the ethylene glycol. Most often, the hydrogenation catalyst comprises copper, either in the elemental form or combined with oxygen. Other representative moieties may include, for example, nickel, cobalt, ruthenium, palladium, platinum, rhodium, rhenium and combinations thereof. Preferred catalysts are the copper-containing catalysts, both unpromoted and promoted with components (e.g., metal oxide) containing chromium, manganese and/or zinc. The amount of catalytically-active moiety, based on total weight of the catalyst, is generally from about 1 to 50%, while a range of about 2 to 20% is preferred, and about 5 to 15% being more preferred.

The catalyst preparation method, i.e., the solute and impregnating medium, may have a substantial effect on the catalytic hydrogenation. As described in co-pending U.S. application Ser. No. 697,928, filed on even date herewith by W. J. Bartley, which is herein incorporated by reference, a catalyst for the preparation of ethylene glycol, with a copper-containing catalyst is prepared by contacting said solid carrier with a copper ammonium carbonate complex medium and reducing the catalytically-active copper moiety to its active copper form.

Carriers are usually porous substances on which the catalytically-active component is deposited. Most preferably, the carriers are substantially inactive or inert. Suitable carriers may comprise one or more of silica, alumina, titania, molecular sieves, diatomaceous earth, activated carbon, silicon carbide, pumice, zeolite and the like. The silica, titania and alumina carriers are preferred, and the silica carrier is especially preferred.

The physical properties of commercially-available silica carriers vary considerably. Examples, along with their physical properties, of silica carriers used in the examples herein and otherwise are given in Table 1 below. Performance of the catalysts may be affected by the physical characteristics of the carrier as described in co-pending U.S. application Ser. No. 697,926, filed on even date herewith by W. J. Bartley, which is herein incorporated by reference. That application discloses a process for the preparation of ethylene glycol in which the carrier is characterized by a relative activity index of at least about 1.0, said relative activity index being defined by the formula, relative activity index = $1.38 + 0.39a + 0.76b + 0.001c + 0.35d - 0.39ab + 0.012bc + 0.003cd$ wherein a is defined as the nominal external surface area of a typical carrier particle (S), expressed in square millimeters per particle units, divided by the volume (V) of the same carrier particle, expressed in cubic millimeters per particle units, minus 1.96 ((S/V)-1.96); b is defined as the pore volume (P) of the carrier, expressed in cc/gram units, minus 0.84 (P-0.84); c is defined as the average pore diameter (D), expressed in Angstrom units, minus 169 (D-169); and d is defined as the macroporosity variable (M) minus 0.24 (M-0.24), wherein the macroporosity variable is assigned a value of 1.0 if said carrier has at least about 20% of its pore volume associated with pores having a diameter of at least about 1000 Angstroms, and a value of zero if said carrier has less than about 20% of its pore volume associated with pores having a diameter of at least about 1000 Angstroms.

The manufacturers' specifications for non-silica matter in some of these silica carriers are shown in Table 2.

TABLE 2

MANUFACTURERS' SPECIFICATIONS NON-SILICA COMPONENTS (weight %)

| IMPURITY | CALSICAT E-361D | UCI[2] T-869 | DAVISON 59 & 952 |
|---|---|---|---|
| $Al_2O_3$ | 0.09 | 2.40 | 0.15[1] |
| $Fe_2O_3$ | 0.04 | 0.20 | 0.04 |
| $Na_2O$ | 0.80 | 0.18 | 0.10 |
| $TiO_2$ | NS* | 0.10 | NS |
| CaO | NS | 0.10 | 0.10 |
| $K_2O$ | NS | 0.72 | NS |
| MgO | NS | 0.10 | NS |
| $SO_4^{-2}$ | NS | 0.06 | 0.05 |

*NS = no specification
[1]Davison-59 contains 0.05% weight $Al_2O_3$.
[2]United Catalysts, see Table 1.

Preparation of the supported catalyst, in accordance with this invention, typically involves several steps: (1) washing the carrier, (2) impregnating/coating the precursor(s) of the catalytically-active moieties on the carrier, (3) drying and/or calcining the impregnated carrier and (4) reducing the precursor of the catalytically-active moiety to its active form.

As noted above, in accordance with this invention, the hydrogenation catalyst activity is enhanced by employing a catalyst carrier having a leachable iron content not greater than about 0.03% (300 ppm), by weight of the carrier. In a more preferred form, the catalyst carrier has a leachable iron content not greater than about 0.01% (100 ppm), by weight of the carrier. Additionally, catalyst activity is optimized by employing a catalyst carrier having a leachable sulfur, expressed as sulfate, content not greater than about 0.04% (400 ppm), by weight of the carrier. In a more preferred form, the catalyst carrier has a leachable sulfur, expressed as sulfate, content not greater than about 0.02% (200 ppm), by weight of the carrier.

The degradation of silica carriers by reactants and/or products is generally minimized by employing a catalyst carrier having a leachable alkali metal content not greater than, say, about 0.03% (300 ppm), by weight of the carrier. In a more preferred form, the catalyst carrier has a leachable alkali metal content not greater than about 0.01% (100 ppm), by weight of the carrier.

Leachable is defined as that component, e.g., iron, that can be extracted and/or removed from the surface of the carrier. This term does not include the total iron concentration of the carrier, i.e., the leachable iron plus the bound iron, as the extraction of bound iron is not necessary because such iron is not believed to provide adverse effects during the utilization of the catalyst carrier.

TABLE 1

PHYSICAL PROPERTIES - COMMERCIAL SILICA CARRIERS[a]

| SUPPLIER | SUPPLIER'S IDENTIFICATION | CARRIER PARTICLE SIZE, (mm) | SURFACE AREA, ($m^2/g$) | AVG. PORE DIAMETER, (Å) | CRUSH STRENGTH (lbs.) | PORE VOLUME (cc/g) |
|---|---|---|---|---|---|---|
| Calsicat | Silica 300 | 4.8 × 4.8 | 100 | 300 | 13 | 0.76 |
| Calsicat | Silica 7000 | 4.8 × 4.8 | 3 | 7000 | 16 | 0.50 |
| Davison | Grade 59 | 2.4–6.4 | 300 | 95 | [d] | 1.20 |
| Davison | SMR 7-6245-2 | 4.8 × 4.8 | 128 | 193 | 25 | 0.62 |
| Davison | SMR 7-6204-2 | 7.9 × 7.9 | 96 | 220 | 28 | 0.63 |
| Davison | SMR 7-6204-1 | 4.8 × 4.8 | 155 | 130 | 20 | 0.68 |
| Davison | SMR 7-6230-1 | 4.8 × 4.8 | 245 | 90 | 20 | 0.62 |
| Davison | Grade 952[b] | 1–2 | 300 | 120 | [d] | 1.65 |
| Calsicat | E-361D | 3.2 × 3.2 | 20 | 700 | 17 | 0.69 |
| Cabosil | M-5[b] | 1–2 | 200 | NA[c] | [d] | NA[c] |
| United Catalysts | UCI, T-869 | 3.2 × 3.2 | 68 | 1700 | 8 | 0.43 |
| Norton | HSA 16188 | 4.8 × 4.8 | 220 | 180 | 8 | 0.99 |

[a]as found by applicant
[b]supplied as a powder, pelleted by applicant
[c]NA = Not applicable
[d]very low Frequently, it is desirable to pretreat the carrier, e.g., by washing to remove significant amounts of extraneous leachable components that may be deleterious to the performance of the catalyst. Conveniently, the washing may be with an acid solution. Any suitable acid treatment (washing) technique may be utilized. An especially preferred acid for the treatment is oxalic acid. According to the present invention, the carrier material may be treated (washed) with an aqueous acid solution by any means of contact. Typically, soaking with or without agitation, along with a means for continually draining the aqueous acid solution is desired, although the invention can be practiced by batch operation. Contact time may vary from about one to about fifty hours, with about five to about fifteen hours being preferred. The volume of aqueous acid solution to carrier material typically ranges between about 1 and about 100 volumes with about 10 to about 20 volumes being preferred. The temperature of the aqueous acid solution may range from about room temperature (20° C.) to the boiling point of the aqueous acid solution. An elevated temperature facilitates the removal of iron and/or sulfur, and a temperature ranging from about 70° C. to about 100° C. is preferred. The aqueous acid solution may contain any acid effective in removing iron and/or sulfur. Strong acids, for example, hydrochloric acid, sulfuric acid, nitric acid and phosphoric acid, typically can be employed. Additionally, organic acids may be utilized. Suitable organic acids include chloroacetic acid, trichloroacetic acid, maleic acid, lactic acid, formic acid and malonic acid and the like, with oxalic acid being preferred. Typically, acid concentrations between about 1% and about 50%, by weight, may be employed, with concentrations between about 10% and 40%, by weight, being preferred. The aqueous acid solution may contain materials other than acid, such as reducing agents or materials capable of elevating the boiling point of the aqueous acid solution. For example, glycerine is preferably used to elevate the boiling point of the preferred aqueous oxalic acid solution. After sufficient contact time to accomplish removal of iron and/or sulfur, the carrier material is typically washed with distilled water. This washing is typically accomplished with between about one and about 100 volumes of water to about one volume of carrier material, with washing solution volumes of about 20 to about 30 to about one volume of carrier material being preferred. After washing, the carrier material is typically dried. Drying can be accomplished at room temperature or preferably at elevated temperatures until the carriers are substantially dry. Temperatures ranging from about 70° C. to about 200° C., may be utilized, with temperatures ranging between about 110° C. to about 150° C. being preferred. Preferably, the drying conditions are sufficiently mild so that no unduly adverse effects to the carrier occur.

Any means of depositing the catalytic metal components on the carrier, e.g., impregnating or coating techniques, may be used. Any effective impregnation treatment or solute may be utilized to impregnate the carrier. Typically, the carrier is impregnated with a medium containing a precursor which is decomposable to the catalytically-active moiety in the final catalyst. Thus, for example, where the desired active moiety is copper, a copper salt, such as copper nitrate, or a copper complex, such as a copper ammonia complex, may conveniently be used as the solute, and then the precursor can be converted to the desired active moiety. Where the desired active material is a material other than copper, a decomposable salt of the desired metal is chosen as the solute of the impregnating solution. In general, the desired active moiety is a metal, or a mixture of metals, and the solute or decomposable compound is correspondingly a metal salt, metal oxide or metal hydroxide or a mixture of metal salts, oxides or hydroxides.

Performance of the catalyst may be affected by the nature of the impregnating solution, i.e., the solute and the impregnating medium, as described in copending U.S. application Ser. No. 697,928 of W. J. Bartley.

After impregnation, the carrier with deposited catalytically-active moiety or precursor can be dried, or, if a decomposable precursor is used, it can be converted to the desired catalytically-active form. Usually, drying and decomposition are separate operations, since most decomposable precursors will not be decomposed under normal drying conditions. Drying typically can be accomplished by exposure to drying conditions including elevated temperatures ranging from about 50° C. to about 200° C., for several hours, e.g., 0.5 to 30 hours, with temperatures ranging from about 75° C. to about 150° C. being preferred. Preferably, the drying conditions are sufficiently mild so that no unduly adverse effects to the carrier occur.

In some instances, when the decomposable precursor is a salt, it may be desired to form the oxide by calcination to facilitate the formation of the metal (should that be the desired catalytically-active moiety) through reduction. Calcination involves high temperature heating under oxidizing conditions so that any hydrates, carbonates, or the like are decomposed and volatile material is expelled. Calcination in an air atmosphere is a preferred means of converting most decomposable precursors to the oxide of the metal. The calcination treatment will usually depend on the decomposable precursor. For example, a copper salt, such as copper nitrate, begins decomposing to the copper oxide at about 170° C. Copper carbonate, on the other hand, does not begin to decompose until a temperature of about 200° C. In general, calcination typically can be carried out by exposure to temperatures ranging from about 170° C. to about 600° C. depending on the catalyst precursor for a time sufficient to allow substantial conversion to the metal oxide form, with temperatures in the range of about 200° C., to about 500° C. being preferred.

Where the desired catalyst has a metal rather than a metal oxide as its catalytically-active moiety, the catalyst may then be reduced to the metal form by treatment with hydrogen prior to hydrogenation or during the hydrogenation reaction. Other reducing agents, e.g., carbon monoxide and metal hydrides, can also be employed. Reduction prior to the hydrogenation reaction typically involves purging the catalyst with an inert gas to remove oxygen and reducing under conditions that include the presence of reducing agent and elevated temperatures.

Actual reduction procedures will vary depending on the catalyst and catalytically-active moiety. Hydrogen reductions of copper oxide to copper metal are typically carried out at temperatures ranging from about 100° C. to about 300° C. with hydrogen partial pressures ranging from about 0.001 to about 100 bars in the substantial absence of oxygen. A slow reduction time is preferred and therefore preferred temperatures range from about 150° C. to about 250° C. with preferred hydrogen partial pressures ranging from about 0.01 to about 10 bars. Conditions sufficient to convert at least a major portion of the oxide to the metal are preferred, with a conversion of 90% or greater being more preferred.

The following examples are provided to illustrate the present invention in accordance with the principles of this invention, but are not to be construed as limiting the invention.

EXAMPLES

The following discloses the general method employed to prepare and evaluate the catalysts designated in the examples.

1. PREPARATION OF SUPPORTED CATALYSTS

The carriers are washed by slowly and continuously passing a mixture of oxalic acid, glycerine, and water in proportions of 1:1.5:1.1 by weight, respectively, through a loosely packed bed of carrier contained within a glass column which drains through a stopcock at its base. The contents of the column are maintained at about 90° C. throughout the washing procedure. About 10-20 volumes of the solution containing oxalic acid are used to wash one volume of carrier (loosely packed volume) over a five to fifteen-hour period. The carrier material is then washed with about 20-30 volumes of distilled water at about 90° C. over a period of about five to fifteen hours and then dried overnight at about 110°-150° C. in a drying oven.

The carriers are then impregnated. The desired quantities of copper precursor, $CuCO_3$ (basic), calculated to yield a 10% copper concentration in the finished catalyst, are dissolved in an aqueous $NH_4OH$ medium. The volume of $NH_4OH$ is selected to at least fill the pores and to provide a 4 to 1 molar ratio of ammonia to copper. This mixture is allowed to stand at room temperature (about 20° C.) with occasional stirring until most of the solids are dissolved (about 1 to 60 minutes). Heating to 40°-50° C. may be required to dissolve all solids when high copper concentrations are employed.

The carrier is then placed in a vacuum flask. The top of the flask is sealed with a rubber septum, and the flask is evacuated through the side arm. A syringe needle is then used to inject the impregnating solution onto the evacuated carrier material. When the addition is complete, the material is mixed well, then the impregnated carrier is allowed to stand with occasional stirring at ambient pressure (about 1 atmosphere) for approximately 30 minutes at room temperature. It is then dried in a nitrogen atmosphere using the following heat sequence: 85° C. (for 1 hr.); 110° C. (for 2 hrs.); and 150° C. (for 2 hrs.). The impregnated carrier is then calcined at 300° C. for 2 hrs. in an air atmosphere.

To achieve reduction of the copper component, the dried, impregnated carrier is placed in the reactor used for the production of ethylene glycol and heated to 150° C. for 1 hour under flowing nitrogen. Hydrogen is then introduced into the nitrogen stream at a flow rate sufficient to give an atmosphere of about 1-2% hydrogen and a total hydrogen and nitrogen space velocity of about 2000-3000 $hr.^{-1}$ (based on the volume of the catalyst bed). The temperature is increased gradually from 150° C. to 225° C. over an 18-hour period (approximately a 4° C. increase per hour) and then held at 225° C. for 6 hours.

2. PRODUCTION OF ETHYLENE GLYCOL

The hydrogenation of diethyl oxalate is conducted under continuous conditions in a ¾ inch outside diameter by 16 inch stainless-steel tubular reactor (70 milliliters volume) which is coaxially fitted with a ⅛ inch diameter stainless-steel thermocouple well in accordance with the following procedure. A 20 ml charge of catalyst is dispersed with an equal volume of 3/32 inch glass helices and placed in the center of the stainless steel tube reactor with beds of 3/32 inch glass helices fully occupying the space above and below the charged catalyst. After reduction, the temperature and molecular hydrogen flow rate are then adjusted to levels set forth in Table 3 and diethyl oxalate flow is started. Liquid diethyl oxalate is premixed and vaporized with molecular hydrogen at 225° C. in a separate preheater filled with 3/32 inch glass helices and of outside dimensions identical to that of the stainless steel tubular reactor, but with an internal volume of 35 ml. The gaseous reactants are then passed downward over the catalyst bed at conditions of temperature, pressure, and gas and liquid flow rates (gas hourly space velocity and liquid hourly space velocity) as indicated in the examples in the table below. The products are then condensed and collected at reactor pressure. The condensate is analyzed by gas chromatography.

In the examples shown in Table 3, the results of catalytic hydrogenations using carriers subjected to a wash treatment containing oxalic acid are compared with those using unwashed catalyst carriers. The unwashed carriers are representative of commercial carriers having iron and sulfur concentrations greater than about 0.03% and about 0.04%, by weight of the carrier, respectively. The oxalic acid washing removes a significant quantity of iron and sulfur and accounts for the increased hydrogenation activity.

TABLE 3

EFFECT OF OXALIC ACID WASHING ON 10% COPPER CATALYSTS SUPPORTED ON COMMERCIAL SILICA CARRIERS[1]

| CARRIER | WASHED | TEMP., °C.[2] | H2/DEO[3] | LHSV, $hr^{-1}$[4] | % DEO CONV.[5] | EG STY[6] |
|---|---|---|---|---|---|---|
| Davison[a] | No | 211 | 100 | 0.46 | 17 | 0.6 |
| Davison[a] | Yes | 211 | 102 | 0.53 | 63 | 37 |
| UCI[b] | No | 210 | 82 | 0.56 | 50 | 42 |
| UCI[b] | Yes | 210 | 82 | 0.57 | 99.8 | 217 |
| UCI[b] | Yes | 210 | 60 | 0.78 | 99.6 | 300 |
| UCI[b] | Yes | 202 | 85 | 0.55 | 99.7 | 230 |
| Calsicat[c] | No | 210 | 82 | 0.56 | 22 | 6 |
| Calsicat[c] | Yes | 210 | 86 | 0.54 | 100 | 210 |
| Davison[d] | No | 210 | 172 | 0.27 | 79 | 68 |

TABLE 3-continued
EFFECT OF OXALIC ACID WASHING ON 10% COPPER CATALYSTS SUPPORTED ON COMMERCIAL SILICA CARRIERS[1]

| CARRIER | WASHED | TEMP., °C.[2] | $H_2$/DEO[3] | LHSV, $hr^{-1}$[4] | % DEO CONV.[5] | EG STY[6] |
|---|---|---|---|---|---|---|
| Davison[d] | Yes | 210 | 47 | 1.00 | 100 | 420 |

[a]Davison SMR 7-6204-1, surface area = 155 m²/g, average pore diameter = 130 A°, 3/16 inch pellets.
[b]United Catalysts Inc. T-869, surface area = 68 m²/g, average pore diameter = 1700 A°, ⅛ inch extrusions.
[c]Calsicat E-361D, surface area = 20 m²/g, average pore diameter = 700 A°, 3.2 × 3.2 mm pellets.
[d]Davison 952, surface area = 300 m²/g, average pore diameter = 120 A°, 1-2 mm pellets.
[1]Pressure = 30 bars, GHSV = 7500 $hr^{-1}$ (gas hourly space velocity);
[2]Reaction zone temperature;
[3]Mole ratio of hydrogen ($H_2$) to diethyl oxalate;
[4]Liquid hourly space velocity;
[5]Percent diethyl oxalate reacted;
[6]Ethylene glycol, space time yield (grams ethylene glycol/liter catalyst/hour).

In the examples shown in Table 4, catalytic hydrogenations over oxalic acid washed and unwashed "Davison-59" silica carrier catalysts are compared with the catalytic hydrogenations over oxalic acid washed "Davison-59" silica carrier catalysts with $Fe^{+3}$ or $SO_4^{-2}$ impurities added in controlled amounts after the washing treatment to provide a basis for comparison.

The control examples with added impurities are prepared as follows: The "Davison-59" silica carrier is first prewashed with a solution containing oxalic acid and then dried using the procedure described for the examples shown in Table 3 above. After washing and prior to impregnation with the catalyst component, the washed silica carrier is impregnated with a solution of Fe(NO₃)₂ in water to produce the desired, controlled iron concentration.

The concentration is selected to give an iron content ($Fe^{+3}$) of 0.05%, by weight of the carrier. The solution volume is adjusted to just fill the carriers' pores (incipient wetness technique). This iron impregnation is carried out under vacuum using the same impregnation apparatus and general procedure described in the above examples shown in Table 3. After drying and calcination at 85° C. (1 hr.), 110° C. (2 hrs.), 150° C. (2 hrs.), and 300° C. (2 hrs.), the treated carrier is then impregnated to obtain a 10% copper catalyst using the $CuCO_3$ (basic)/concentrated $NH_4OH$ procedure described for the examples shown in Table 3.

The sulfate impurities were similarly added in controlled amounts, as $(NH_4)_2SO_4$ in concentrated $NH_4OH$, except that they are added with the copper carbonate impregnation solution, not prior to it. The $(NH_4)_2SO_4$ concentration is selected to give a sulfur, expressed as sulfate, content of 0.05%, by weight of the carrier.

The data in Table 4 demonstrate that the catalytic activity is greater when oxalic acid washed carriers are utilized as compared to unwashed carriers or carriers with $Fe^{+3}$ or $SO_4^{-2}$ impurities added. The decrease in activity with the addition of 0.05% by weight $Fe^{+3}$ or $SO_4^{-2}$ indicates that this minimal concentration level is sufficient to affect adversely catalyst activity.

3. MEASUREMENT OF SILICA DEGRADATION

During normal catalyst testing, several hundred hours of operation are generally required to give a measurable silica loss and produce a noticeable effect on catalyst crush strength. For this reason, an accelerated testing procedure is utilized. The accelerated testing is accomplished by passing methanol vapors over crushed silica pellets (1–2 mm) at temperatures of 300° C. to 400° C. Continuous conditions and atmospheric pressure are employed. Gas chromatographic analysis of the methanol condensate after contact with silica carrier material demonstrates the presence of methyl orthosilicate $(CH_3O)_4Si$ as a reaction product. After hydrolysis of the organosilicon products with 50% aqueous sulfuric acid, the $SiO_2$ concentration (the amount of degraded silica) is determined by gravimetric analysis.

The silica degradation testing is performed using a 1½-inch by 18-inch glass tubular reactor. In operation, the tube is charged with 10 to 20 grams of 8–14 mesh silica which is placed between beds of 8 to 14 mesh Filtrose. The volumes of the Filtrose layers are selected so as to completely fill the reactor tube. The system is heated to the desired operating temperature under a 0.5 to 1 liter/hr. flow of nitrogen to remove traces of moisture. After heating and purging 30 to 40 minutes in this fashion, the nitrogen flow is discontinued. Methanol is then pumped to the system at a rate of 10 to 30 ml/hr., and the contents of the product receiver are collected every one to two hours.

In some experiments, the methanol condensate solution is first analyzed by gas chromatography using a FID detector and a 6'×⅛" column packed with 10% CARBOWAX 20 M ™ polyethylene glycol available from Union Carbide Corp., Danbury, Ct, U.S.A., (TPA) on CHROMOSORB T ™. The oven temperature is held at 60° C. for 5 minutes and then programmed to 250° C. at 10° C./min. under 30 ml/min. helium flow. The presence of tetramethyl orthosilicate, which elutes at 6.9 minutes, is verified by cochromatography with an authentic sample of tetramethyl orthosilicate, and by gas chromatography/mass spectrometry. After verification, hydrolysis of the organosilicon products is accomplished in order to quantify the $SiO_2$ concentration, which is carried out by gravimetric analysis.

The Norton HSA 16188 carrier, designated (A) in Table 5, is utilized as received from the manufacturer, unwashed. The Norton HSA 16188 carrier, designated (B) in Table 5, is washed utilizing the procedure given in the section entitled "Preparation of Supported Catalysts" prior to testing. The Norton HSA 16188 carrier, designated (C) in Table 5, is not washed and is impregnated with 0.5% sodium acetate. The impregnation of the carrier is accomplished by placing 10 grams of the unwashed silica carrier material in a flask and adding a solution of 0.178 grams of sodium acetate in 11 ml of water. This mixture is mixed well until all the liquid is absorbed. The mixture stands for 30 minutes at room temperature and is subsequently dried at 85° C. for 2 hrs., at 110° C. for 2 hrs., and at 150° C. for 2 hrs.

As shown in Table 5, the silica degradation rate, i.e., the rate of silica loss and, hence, loss of crush strength, increases significantly with temperature and with the level of alkali metal(s), in particular sodium, in the carrier material.

TABLE 4

EFFECT OF ADDED IMPURITIES ON 10% COPPER CATALYSTS SUPPORTED ON COMMERCIAL SILICA CARRIERS

| ADDITIVE[1] | WASHED[2] | $H_2$/ DEO[3] | LHSV $(hr^{-1})$[4] | % DEO CONV.[5] | EG. PROD.[6] |
|---|---|---|---|---|---|
| None | Yes | 41 | 1.15 | 100 | 7.7 |
| $SO_4^{-2}$ | Yes | 47 | 1.00 | 100 | 6.7 |
| $Fe^{+3}$ | Yes | 54 | 0.88 | 99.7 | 5.1 |
| None | No | 63 | 0.76 | 98.1 | 4.3[7] |

[1]All additives at 0.05%, by weight of the carrier. Catalytic hydrogenation at 210° C. reactor temperature, 30 bars, and GHSV (gas hourly space velocity) of 7600–7700 hr.$^{-1}$, with a 10% Copper/Davison-59 $SiO_2$ catalyst (1 -2 mm particle size).
[2]Carriers were washed prior to the addition of impurities.
[3]Mole ratio of hydrogen ($H_2$) to diethyl oxalate.
[4]Liquid hourly space velocity. To assure that the diethyl oxalate conversions are similar, the LHSV's are adjusted to give a similar ethyl glycolate breakthrough (about 4% selectivity, based on total products, unless otherwise noted).
[5]Percent diethyl oxalate reacted.
[6]Ethylene glycol productivity (moles ethylene glycol/liter catalyst/hour).
[7]Ethyl glycolate selectivity, 11%, based on total products.

TABLE 5

DEGRADATION OF SILICA CARRIERS BY METHANOL

| Carrier/(Treatment)[1] | Temp. (°C.) | $SiO_2$ Production Rate, (mg/liter/hr.)[2] |
|---|---|---|
| (a) Norton HSA 16188 (unwashed) | 400 | 217 |
|  | 350 | 19.8 |
|  | 300 | 4.1 |
| (b) Norton HSA 16118 (washed) | 400 | 26.5 |
|  | 350 | 17.3 |
|  | 300 | 0.9 |
| (c) Norton HSA 16118 (unwashed and 0.5% NaOAc) | 400 | 859 |
|  | 350 | 558 |
|  | 300 | 383 |

[1]All carriers are 8-14 mesh. The liquid hourly space velocity (LSHV, hr.$^{-1}$) of methanol is 0.69.
[2]The rate of silica degradation is expressed in terms of the total $SiO_2$ content of the organosilicon product in the methanol effluent per liter of carrier per hour, after hydrolysis of the organosilicon products. These values were obtained by gravimetric analysis.

I claim:

1. A process for the preparation of ethylene glycol comprising the steps of contacting, in the vapor phase, hydrogen with at least one of di(lower alkyl)oxalate and lower alkyl glycolate in the presence of a hydrogenation catalyst comprising from about 1 to about 50% by weight, based on the total weight of the catalyst, of copper and a silica carrier, wherein the carrier has a leachable iron content not greater than 0.03% by weight of the carrier.

2. The process of claim 1 wherein the leachable iron content of said carrier has been reduced by treatment with an aqueous acid solution, from a value greater than about 0.03%, by weight of the carrier, to a value not greater than about 0.03%, by weight of the carrier.

3. The process of claim 2 wherein the aqueous acid solution comprises oxalic acid.

4. The process of claim 2 wherein the aqueous acid solution comprises glycerine.

5. The process of claim 1 wherein said lower alkyl is methyl or ethyl.

6. The process of claim 1 wherein the temperature is about 150° C. to 300° C., the pressure about 1 bar to 350 bars, the molar ratio of hydrogen to oxalate ester fed to the reaction zone about 4:1 to 200:1, and the gas hourly space velocity about 2,000 hr.$^{-1}$ to 25,000 hr.$^{-1}$ and the liquid hourly space velocity about 0.1 hr.$^{-1}$ to 3.0 hr.$^{-1}$.

7. A process for the preparation of ethylene glycol comprising the steps of contacting, in the vapor phase, hydrogen with at least one of di(lower alkyl)oxalate and lower alkyl glycolate in the presence of a hydrogenation catalyst comprising from about 1 to about 50% by weight, based on the total weight of the catalyst, of copper and a silica carrier, wherein the copper has a leachable sulfur, expressed as sulfate, content not greater than about 0.04%, by weight of the carrier.

8. The process of claim 7 wherein the leachable sulfur, expressed as sulfate, content of said carrier has been reduced by treatment with an aqueous acid solution, from a value greater than about 0.04%, by weight of the carrier, to a value not greater than about 0.04%, by weight of the carrier.

9. The process of claim 8 wherein the aqueous acid solution comprises oxalic acid.

10. The process of claim 8 wherein the aqueous acid solution comprises glycerine.

11. The process of claim 9 wherein said lower alkyl is methyl or ethyl.

12. The process of claim 7 wherein the temperature is about 150° C. to 300° C., the pressure about 1 bar to 350 bars, the molar ratio of hydrogen to oxalate ester fed to the reaction zone about 4:1 to 200:1, and the gas hourly space velocity about 2,000 hr.$^{-1}$ to 25,000 hr.$^{-1}$ and the liquid hourly space velocity about 0.1 hr.$^{-1}$ to 3.0 hr.$^{-1}$.

13. A process for the preparation of ethylene glycol comprising the steps of contacting, in the vapor phase, hydrogen with at least one of di(lower alkyl)oxalate and lower alkyl glycolate in the presence of a hydrogenation catalyst comprising from about 1 to about 50% by weight, based on the total weight of the catalyst, of copper and a silica carrier, wherein the carrier has a leachable alkali metal content not greater than about 0.03%, by weight of the carrier.

14. The process of claim 13 wherein the leachable alkali metal content of said carrier has been sufficiently reduced by treatment with an aqueous acid solution to enhance the physical stability of the catalyst in the process.

15. The process of claim 14 wherein the aqueous acid solution comprises oxalic acid.

16. The process of claim 14 wherein the aqueous acid solution comprises glycerine.

17. The process of claim 13 wherein said lower alkyl is methyl or ethyl.

18. The process of claim 13 wherein the temperature is about 150° C. to 300° C., the pressure about 1 bar to 350 bars, the molar ratio of hydrogen to oxalate ester fed to the reaction zone about 4:1 to 200:1, and the gas hourly space velocity about 2,000 hr.$^{-1}$ to 25,000 hr.$^{-1}$ and the liquid hourly space velocity about 0.1 hr.$^{-1}$ to 3.0 hr.$^{-1}$.

19. A process for the preparation of ethylene glycol comprising the steps of contacting, in the vapor phase, hydrogen with at least one of di(lower alkyl)oxalate and lower alkyl glycolate in the presence of a hydrogenation catalyst comprising from about 1 to about 50% by weight, based on the total weight of the catalyst, of copper and a silica carrier, wherein the carrier has a leachable iron content not greater than 0.03%, by weight of the carrier, a leachable sulfur content, expressed as sulfate, not greater than 0.04%, by weight of the carrier, and a leachable alkali metal content sufficiently low so as to enhance the physical stability of the catalyst in the process.

20. The process of claim 19 wherein the leachable iron content, the leachable sulfur, expressed as sulfate, content, and the leachable alkali metal content of said carrier has been reduced by treatment with an aqueous acid solution, from a value greater than about 0.03%, about 0.04% and about 0.03%, respectively, by weight of the carrier, to a value not greater than about 0.03%, about 0.04% and about 0.03%, respectively, by weight of the carrier.

21. The process of claim 20 wherein the aqueous acid solution comprises oxalic acid.

22. The process of claim 20 wherein the aqueous acid solution comprises glycerine.

23. The process of claim 19 wherein said lower alkyl is methyl or ethyl.

24. The process of claim 19 wherein the temperature is about 150° C. to 300° C., the pressure about 1 bar to 350 bars, the molar ratio of hydrogen to oxalate ester fed to the reaction zone about 4:1 to 200:1, and the gas hourly space velocity about 2,000 hr.$^{-1}$ to 25,000 hr.$^{-1}$ and the liquid hourly space velocity about 0.1 hr.$^{-1}$ to 3.0 hr.$^{-1}$.

* * * * *